United States Patent [19]
Kobayashi

[11] Patent Number: 5,430,538
[45] Date of Patent: Jul. 4, 1995

[54] APPARATUS TO ASSIST IN THE QUALITATIVE EVALUATION OF FACETED GEMS

[75] Inventor: Hiroaki Kobayashi, Tokyo, Japan

[73] Assignee: Taico Co., Ltd., Japan

[21] Appl. No.: 165,167

[22] Filed: Dec. 10, 1993

[30] Foreign Application Priority Data

Dec. 18, 1992 [JP]  Japan .................. 4-356055

[51] Int. Cl.[6] ........................................ G01N 21/01
[52] U.S. Cl. ........................................ 356/30
[58] Field of Search .............. 356/30, 31, 416, 419

[56] References Cited
U.S. PATENT DOCUMENTS 4,884,887  12/1989  Vanderwater ............... 356/31
5,196,966   3/1993  Yamashita ................... 356/30
5,298,963   3/1994  Moriya et al. ............... 356/31

*Primary Examiner*—Richard A. Rosenberger
*Attorney, Agent, or Firm*—Nixon & Vanderhye

[57] ABSTRACT

Apparatus for assisting in the qualitative evaluation of facted gems (i.e., gems having cut facets formed thereon), which magnifies the radiance of cut facets illuminated by colored light beams so as to allow direct viewing or the formation of a color image which can be expressed on a video screen and/or a video printer. The beauty of a gem at the time of its appraisal and sales is thereby increased by use of the apparatus which thereby contributes to gem appraisal and sales by arousing customer interest.

20 Claims, 3 Drawing Sheets

APPARATUS TO ASSIST IN THE QUALITATIVE EVALUATION OF FACETED GEMS

FIELD OF INVENTION

The present invention relates to a magnifying apparatus for gems having cut facets (such as cut diamonds and the like) therein which allows viewing, photographing or the obtaining of a print-out from a video printer following magnification of the border lines between cut facets of the gem, by coloring each of the cut facets with the reflected or transmitted light of colored light beams.

BACKGROUND OF THE INVENTION

In conventional magnifying apparatus for gems having cut facets, the gem is illuminated with white light using a dark field illumination apparatus. Images of the cut facets of a gem produced by this radiated light beam are then reproduced with a magnifier, video display or video printer. The following provides an explanation of a conventional apparatus using a video display or video printer, which has been used quite frequently in recent years. The conventional dark field illumination apparatus in FIG. 6 is provided with a forming opening 2 in the upper surface of case 1. A douser 4 is installed between the light source lamp 3 and the opening 2 so that the light beams of the light source lamp 3 installed within case 1 do not reach opening 2 directly. The inner surface of case 1 is furthermore made to reflect the light beams of light source lamp 3.

Gem 5, such as a diamond, wherein cut facets are formed, is attached by support arms at the upper portion of the opening 2, and video camera 6 for photographing this gem 5 is installed on the opposite side from opening 2.

Thus, the light beams emitted from light source lamp 3 do not reach gem 5 directly, but rather only light beams reflected on the inner surface of case I illuminate gem 5. These light beams are then photographed by video camera 6 corresponding to the state of the cuts of the gem, magnified and then reproduced with a video display or video printer.

The quality of the cuts of the gem, the presence of impurities within the gem and transparency can be evaluated using this image depicted on the video display or video printer, thereby allowing appraisal and ranking of the gem.

In this type of magnifying apparatus for gems having cut facets formed therein, since the light and dark pattern of white light according to the cuts of the gem is only produced on a video display or printed out with a video printer, the border lines of adjacent cut facets are not shown. Thus, it is difficult to evaluate the quality of the gem, and particularly gem proportions and the ranking of its cut. In addition, it also has the disadvantage of having difficulty in adequately arousing the interest of customers during sales of gems and so forth.

SUMMARY OF THE INVENTION

In order to eliminate the above-mentioned disadvantages, the object of the present invention is to provide a magnifying apparatus for gems having cut facets formed therein that allows evaluation of major symmetry to be performed easily by persons other than experts during gem appraisal, and particularly during evaluation of the cut, by magnifying the gem and dividing the radiance of the cut facets according to color by a plurality of colors of light beams, and either viewing the gem directly or representing the image of the gem with a video display or video printer, while also contributing to gem sales by arousing interest in customers as a result of enhancing the beauty of the gem at the time of gem sales.

Optic lenses used in means for magnifying extremely small objects such as gems as in the present invention have an extremely narrow focusing range so that at a distance even slightly outside that focal distance, the images at that location are not connected, with only the image at that focal distance being produced.

Gems such as diamonds that are appraised and so forth by magnifying have high light beam transmissivity so that by connecting the images of the above-mentioned optic lens within that gem, it is possible to view the image of the light beams that strike the gem at that location.

The magnifying apparatus for gems having cut facets formed therein of the present invention radiates different colors of light beams onto the surface of a gem by means of an illumination means that illuminates a gem supported by a support means using a light source divided into a plurality of different colors in the circumferential direction surrounding the gem.

The image at which light beams that have struck the cut facets of a gem illuminated by these light beams connect at the focal position of an optic lens by transmission or reflection is reproduced by individually coloring the cut facets with a reproduction means such as viewing directly with a magnifier or photographing with a color video camera and either viewing by displaying the photographed image on the monitor screen or a color video camera or printing out with a color video printer. In particular, since the borders between cut facets are distinguished by color, an image is formed in the manner of a mosaic pattern.

BRIEF DESCRIPTION OF THE ACCOMPANYING DRAWINGS

DETAILED DESCRIPTION OF THE PREFERRED EXEMPLARY EMBODIMENTS

Figure 1:
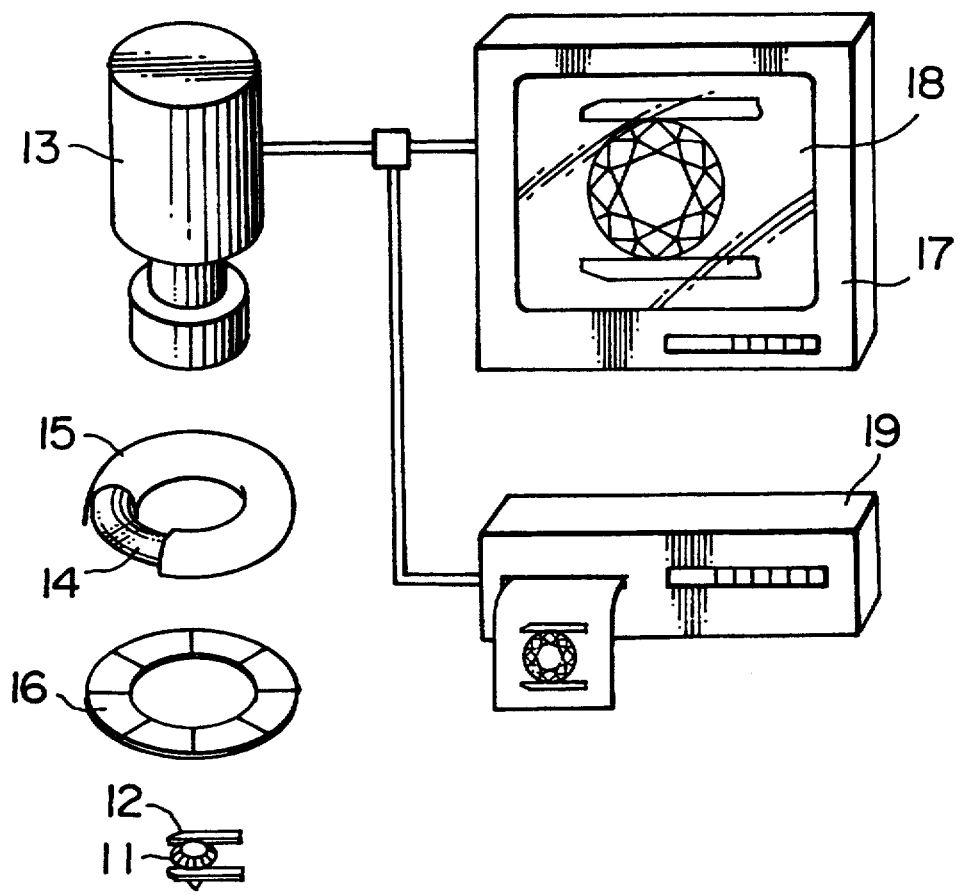
FIG. 1 is a conceptual drawing of a first embodiment of the present invention.
Figure 2:
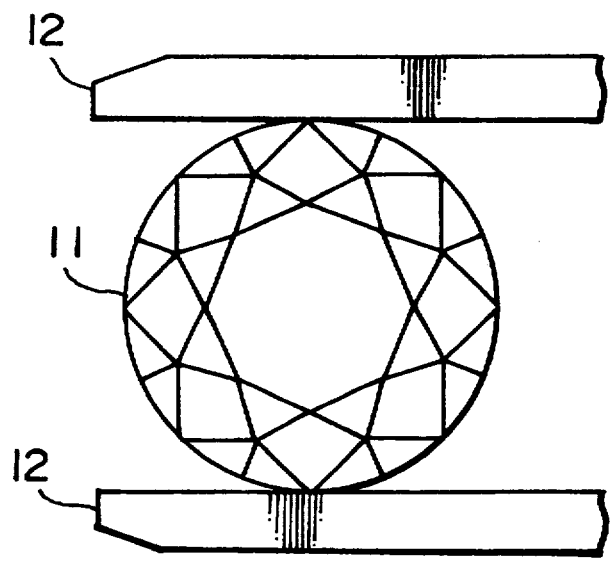
FIG. 2 is a top view of the diamond support means of the above-mentioned embodiment.
Figure 3:
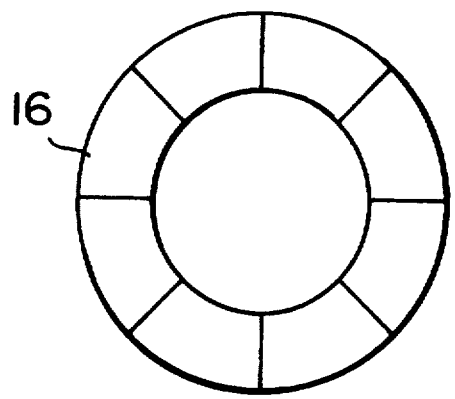
FIG. 3 is a top view of a light source and a color filter with a portion removed.

The following provides an example of the embodiments of the present invention in the case of magnifying a diamond with reference to FIGS. 1 through 3.

In this embodiment, support means 12 which supports diamond 11 pinches diamond 11 from both sides to allow light beams to freely enter from the surface of diamond 11 as well as to allow reflected light of its cut facets to be viewed through diamond 11 from above.

Color video camera 13 is installed above this support means 12 on the same center line as diamond 11 held with said support means 12, and the optic lens of this color video camera 13 is able to connect the focal points on not only the upper surface of diamond 11 but also to its inside due to the transparency of diamond 11.

A ring-shaped light source 14 is provided around this color video camera 13, and cover 15 is provided on this light source 14 so that light beams are only able to be radiated onto diamond 11 located beneath it. Doughnut-shaped color filter 16 is provided on the light beam radiating side of this cover 15 wherein, together with its circumference being divided into a plurality of sections, the surface of each divided section is given a different color.

Thus, although light beams emitted from light source 14 are only able to be transmitted in the direction of diamond 11 supported with support means 12, as a result of passing through color filter 16 at that time, different colors are produced according to the direction of incidence of said light beams at the time of entry into said diamond 11.

Light beams having different colors according to this direction of incidence are reflected in colors of incidence respectively different for each of the cut facets of diamond 11.

The optic lens of color video camera 13 which photographs these colors should have a short focal distance, a large magnification factor and a narrow focusing range.

Moreover, since diamond 11 has high transparency allowing the focal points of the optic lens to be connected within, by aligning the focal points on the cut facets and inside diamond 11 to be magnified, the reflected colors produced by each cut facet of those focal positions can be captured. The images of other cut facets cannot be captured as video images due to excessive obscurity caused by differences in focal distance.

Thus, by changing the focal position or magnification factor of this optic lens, color video camera 13 is able to capture different colored reflected images of cut facets of different heights, and video apparatus 17, having a monitor screen 18, and video camera printer 19 are connected to this color video camera 13.

Consequently, the above-mentioned image can be displayed on monitor screen 18 of video apparatus 17 or printed out with video color printer 19. Moreover, images of each of the cut facets can be viewed by changing the focal distance of the optic lens of color video camera 13.

In addition, different cut facets can be made to appear in different colors depending on the degree of alignment with the colored incident light beams. As a result, the borders between cut facets can be clearly viewed thus allowing the appraisal for evaluating the symmetry of the cuts of diamond 11 or appraisal or the quality and so forth of the cut state.

In addition, since the images are produced in color, the image may appear in the form of a heart or arrow depending on the focal position or inclination (upward or downward inversion) of the diamond.

Figure 4:
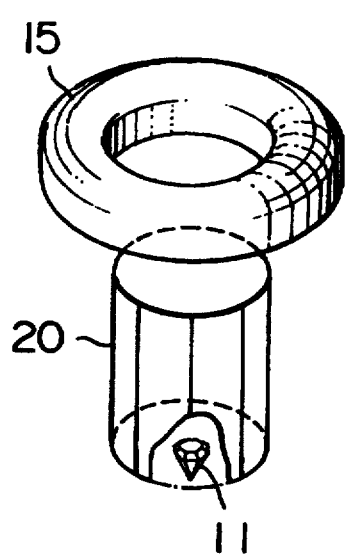
FIG. 4 is a conceptual drawing of a second embodiment of the present invention including a cutaway portion showing a diamond.

The following provides an explanation of another embodiment of the present invention with respect to FIG. 4. In this embodiment, since the illumination means which radiates light beams of different colors in a radial pattern is the only aspect that differs from the previous embodiment, the explanation will focus primarily on this illumination means.

Translucent cylinder 20 made of acrylic and so forth, the circumferential surface of which is divided into a plurality of sections parallel to a center line to form different colors, is provided on light source 14 of this embodiment around color video camera 13 in the same manner as the previous embodiment and in the direction in which light beams are emitted from its cover 15.

Support means 12 which supports diamond 11 is provided at the location at which light beams are radiated from light source 14 which have passed through cylinder 20 in the same manner as the previous embodiment in the vicinity of the end surface of the opposite side from color video camera 13 of this cylinder 20.

Thus, in this embodiment as well, light beams of different colors are radiated from the surface onto diamond 11, and the images of the cut facets of diamond 11 produced by these light beams are captured by color video camera 13 through the hollow space of cylinder 20, thus allowing the performing of various appraisals in the same manner as the previous embodiment.

Figure 5:
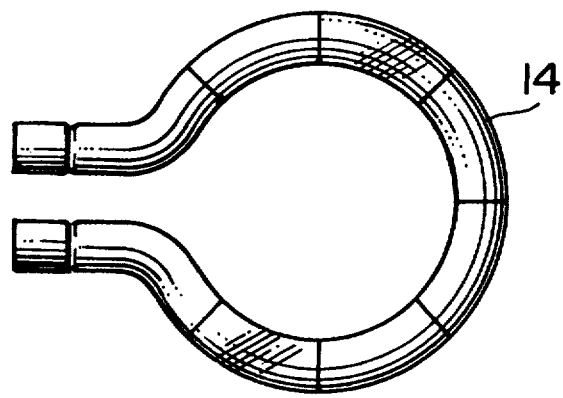
FIG. 5 is a top view of the light source of a third embodiment of the present invention.
Figure 6:
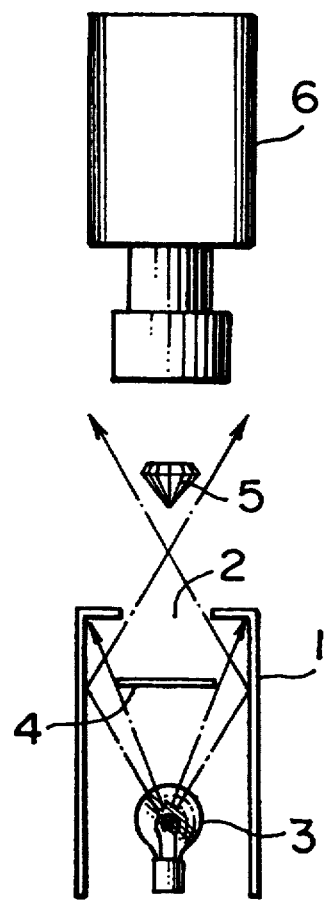
FIG. 6 is a drawing illustrating the principle of a dark field illumination apparatus of the prior art.

Moreover, the following provides an explanation of still another embodiment of the present invention with respect to FIG. 5. In contrast to light source 14 and color filter 16 being formed as separate units in the first embodiment, in this embodiment, light source 14 itself is divided into different colors in the radial direction as shown in FIG. 5. However, its action and effects are no different from those of said first embodiment.

Furthermore, support means 12 which supports a gem in the above-mentioned embodiments may be in the form of a gem case which supports the gem vertically. In addition, the magnifying means may be a magnifier such as a microscope used in place of the above-mentioned color video camera 13 that allows the gem to be viewed directly. Moreover, the gem is not limited to a diamond, but rather appraisals similar to those described above can be performed on any gem provided it has cuts formed in its surface.

As described above, the present invention allows light of different colors, reflected from each of the cut facets of a gem by radiating light beams respectively divided into different colors onto the surface of said gem, to be viewed directly or formed into a color image, magnified and photographed as the image of the focal position of an optic lens of a color video camera, and displayed on a video screen or printed out with a video printer to express that image.

Thus, by installing the present invention in a store and providing an explanation to customers desiring to purchase a gem while showing them the image of that gem, together with arousing interest in those customers, since the quality of the gem can be explained in color, the present invention contributes to sales as a result of heightening the desire to purchase on the part of customers, thus offering a first advantage of the present invention. In addition, as a result of color being added to this magnified view at the time of gem appraisals and so forth, the accuracy of gem appraisals can be improved, thus offering a second advantage of the present invention.

What is claimed is:

1. Apparatus to assist in the qualitatively evaluation of a faceted gem comprising:
   a holder for holding a faceted gem to be evaluated to thereby establish an evaluation center line of the faceted gem;
   a magnifying device positioned in spaced relationship to said holder in coaxial alignment with said evaluation center line for magnifying light transmitted from said faceted gem along said evaluation center line and presenting a visual image of the faceted gem based on such transmitted and magnified light;

a light source positioned between said holder and said magnifying device for emitting light toward the faceted gem; and a color filter interposed between said light source and said faceted gem for transforming the light emitted by said light source into a spectrum of differently colored light which illuminates the faceted gem held by said holder, wherein said spectrum of differently colored light is reflected by the faceted gem and transmitted to said magnifying device which responsively depicts a visual image of the faceted gem such that facets of the gem are individually presented in different respective colors to allow borders between adjacent facets to be distinguishable visually based on such different respective colors and thereby permit qualitative evaluation of the faceted gem.

2. Apparatus as in claim 1, wherein said light source annularly surrounds said evaluation center line.

3. Apparatus as in claim 2, wherein said light source includes a cover positioned between said light source and said magnifying device so that light emitted by said light source radiates only toward the faceted gem held by said holder.

4. Apparatus as in claim 1, 2 or 3, wherein said color filter annularly surrounds said evaluation center line.

5. Apparatus as in claim 4, wherein said color filter is disc-shaped.

6. Apparatus as in claim 4, wherein said color filter is cylindrically shaped.

7. Apparatus as in claim 4, wherein said color filter is integral with said light source.

8. Apparatus as in claim 1, wherein said magnifying device is a color video system.

9. Apparatus as in claim 8, wherein said color video system includes, a color video camera coaxially positioned along said evaluation center line and a color display system operatively connected to said color video camera so as to receive color video signal therefrom.

10. Apparatus as in claim 9, wherein said color display system includes at least one of a color video printer, and a color video monitor.

11. Apparatus for assisting in the qualitative evaluation of faceted gems comprising:

holding means for holding the faceted gem coaxially relative to an evaluation center line;

light source means for emitting light toward the faceted gem held by said holding means;

color filter means interposed between said light source means and said holding means for dividing the light emitted by said light source means into a spectrum of differently colored light which illuminates the faceted gem held by said holding means; and magnifying means positioned in spaced relationship to said holding means at a focal position of said differently colored light which is incident upon individual facets of said faceted gem for responsively depicting a visual image of the faceted gem such that the individual facets of the gem are presented in different respective colors to allow borders between adjacent facets to be distinguishable visually based on such different respective colors and thereby permit qualitative evaluation of the faceted gem.

12. Apparatus as in claim 11, wherein said light source means annularly surrounds said evaluation center line.

13. Apparatus as in claim 12, wherein said light source means includes a cover means positioned between said light source means and said magnifying means for directing light emitted by said light source means in a direction only toward the faceted gem held by said holding means.

14. Apparatus as in claim 11, 12 or 13, wherein said color filter means annularly surrounds said evaluation center line.

15. Apparatus as in claim 14, wherein said color filter means is a disc-shaped color filter.

16. Apparatus as in claim 14, wherein said color filter means is a cylindrically shaped color filter.

17. Apparatus as in claim 14, wherein said color filter means is integral with said light source means.

18. Apparatus as in claim 11, wherein said magnifying means is a color video system.

19. Apparatus as in claim 18, wherein said color video system includes, a color video camera coaxially positioned along said evaluation center line and a color display system operatively connected to said color video camera so as to receive color video signal therefrom.

20. Apparatus as in claim 19, wherein said color display system includes at least one of a color video printer, and a color video monitor.

* * * * *